(12) United States Patent
Titlow

(10) Patent No.: US 11,045,509 B2
(45) Date of Patent: Jun. 29, 2021

(54) TRIBUTYRIN COMPOSITIONS AND METHODS THEREFOR

(71) Applicant: Compound Solutions, Inc., Carlsbad, CA (US)

(72) Inventor: Matthew Titlow, Carlsbad, CA (US)

(73) Assignee: COMPOUND SOLUTIONS, INC., Carlsbad, CA (US)

( * ) Notice: Subject to any disclaimer, the term of this patent is extended or adjusted under 35 U.S.C. 154(b) by 23 days.

(21) Appl. No.: 16/519,434

(22) Filed: Jul. 23, 2019

(65) Prior Publication Data

US 2020/0384043 A1    Dec. 10, 2020

Related U.S. Application Data

(62) Division of application No. 16/434,051, filed on Jun. 6, 2019.

(51) Int. Cl.
| | | |
|---|---|---|
| *A61P 1/00* | (2006.01) | |
| *A61K 35/745* | (2015.01) | |
| *A61K 9/00* | (2006.01) | |
| *A61K 31/194* | (2006.01) | |

(52) U.S. Cl.
CPC .......... *A61K 35/745* (2013.01); *A61K 9/0056* (2013.01); *A61K 31/194* (2013.01)

(58) Field of Classification Search
CPC .... A61K 35/741; A61K 35/74; A61K 35/747; A61K 35/745; A61K 2035/115; A61K 9/0056; A61K 31/194; A61K 9/0095; A61K 31/225; A61K 47/36; A61K 47/40; A23V 2002/00; A23V 2200/3202; A23V 2200/3204; A23V 2200/324; A23V 2200/30; A23V 2200/32; A23V 2250/206; A23V 2250/28; A23V 2250/284; A23V 2250/5116; A23L 33/135; A23L 33/21; A23L 33/10; A23L 33/40; A23L 27/00; A23Y 2220/00; A23Y 2300/00; G01N 2800/06; G01N 2800/065; C12N 1/20; A61P 1/00; A23K 20/158
See application file for complete search history.

(56) References Cited

U.S. PATENT DOCUMENTS

| | | |
|---|---|---|
| 6,217,915 B1 | 4/2001 | Luchansky et al. |
| 2016/0263245 A1 | 9/2016 | Donovan et al. |
| 2018/0250412 A1 | 9/2018 | Lee et al. |

FOREIGN PATENT DOCUMENTS

| | | |
|---|---|---|
| CN | 106721312 A | 5/2017 |
| WO | 2018055388 A1 | 3/2018 |

OTHER PUBLICATIONS

Lindsay et al. Clinical, microbiological, and immunological effects of fructo-oligosaccharide in patients with Crohn's disease. Gut. 2006;55(3):348-55.*
Durk et al., "Gut Microbiota Composition is Related to Cardiorespiratory Fitness in Healthy Young Adults," Int J Sport Nutr Exerc Metab., May 1, 2019; 29(3):249-253.
Koliada et al., "Association between body mass index and Firmicutes/Bacteroidetes ratio in an adult Ukrainian population," BMC Microbiology, 2017; 17(120); 6 pgs.
Martin et al., "Functional Characterization of Novel Faecalibacterium prausnitzii Strains Isolated from Healthy Volunteers: A Step Forward in the Use of F. prausnitzii as a Next-Generation Probiotic," Frontiers in Microbiology, Jun. 2017; 8(1226), 13 pgs.
Pandey et al., "Probiotics, prebiotics and synbiotics—a review," J Food Sci Technol, Dec. 2015; 52 (12):7577-7587.
Ridaura et al., "Cultured gut microbiota from twins discordant for obesity modulate adiposity and metabolic phenotypes in mice," Science, Sep. 6, 2013; 341(6150):22 pgs.
Riviere et al., "Bifidobacteria and Butyrate-Producing Colon Bacteria: Importance and Strategies for Their Stimulation in The Human Gut," Frontiers in Microbiology, Jun. 28, 2016; 7(979); 21 pgs.
Riviere et al., "The Ability of Bifidobacteria to Degrade Arabinoxylan Oligosaccharide Constituents and Derived Oligosaccharides Is Strain Dependent," Applied and Environmental Microbiology, Jan. 2014; 80(1):204-217.
Roychowdhury et al., "Faecalibacterium prausnitzii and a Prebiotic Protect Intestinal Health in a Mouse Model of Antibiotic and Clostridium difficile Exposure," JPEN J Parenter Enteral Nutr., Sep. 2018; 42(7)1156-1167.
Tang et al., "The contributory role of gut microbiota in cardiovascular disease," The Journal of Clinical Investigation, Oct. 2014; 124(10):4204-4211.
Wyspianska et al., "Effect of microencapsulation on concentration of isoflavones during simulated in vitro digestion of isotonic drink," Food Sci Nutr., 2019; 7:805-816.
Zheng et al., "Developments in Taste-Masking Techniques for Traditional Chinese Medicines," Pharmaceutics, 2018; 10(157), 22 pgs.
Zhou et al., "Relative Effects of Sensory Modalities and Importance of Fatty Acid Sensitivity on Fat Perception in a Real Food Model," Chem. Percept., 2016; 9:105-119.
Zitvogel et al., "Cancer and the gut microbiota: An unexpected link," Sci Transl Med., Jan. 21, 2015; 9(271); 10 pgs.

(Continued)

*Primary Examiner* — Lynn Y Fan
(74) *Attorney, Agent, or Firm* — Umberg Zipser LLP

(57) ABSTRACT

Tributyrin and/or tributyrin derivatives are used to selectively increase the levels of *Bifidobacteria* in the gut. In preferred methods, the tributyrin and/or tributyrin derivatives are orally administered alone or in combination with a food item or other nutritionally acceptable carrier, and may further include *Bifidobacteria*. Tributyrin-enhanced *Bifidobacterium* strains are also contemplated that include *Bifidobacteria* previously cultured in tributyrin and/or tributyrin derivatives.

7 Claims, 2 Drawing Sheets

(56) References Cited

OTHER PUBLICATIONS

Bedford et al., Implications of butyrate and its derivatives for gut health and animal production, Animal Nutrition, 2018; 4:151-159.
Cresci et al., "Lactobacillus GG and Tributyrin Supplementation Reduce Antibiotic-Induced Intestinal Injury," Journal of Parental and Enteral Nutrition, Nov. 2013; 37(6):763-774.
International Search Report and Written Opinion for International Application No. PCT/US2019/036037 dated Mar. 9, 2020; 12 pgs.

* cited by examiner

TRIBUTYRIN COMPOSITIONS AND METHODS THEREFOR

This application is a divisional application of co-pending US application having Ser. No. 16/434,051, which was filed Jun. 6, 2019.

FIELD OF THE INVENTION

The field of the invention is tributyrin compositions and methods thereof for improving gut health, particularly as it relates to enhancement of *Bifidobacteria* in the gut microbiome.

BACKGROUND

The background description includes information that may be useful in understanding the present invention. It is not an admission that any of the information provided herein is prior art or relevant to the presently claimed invention, or that any publication specifically or implicitly referenced is prior art.

The human gastrointestinal tract harbors an estimated 39 trillion bacterial residents which are commonly referred to as the "gut microbiota" or the "gut microbiome." The specific make-up of these bacterial residents is reported to be intricately related to health and wellness. Specific changes in the composition of the gut microbiota have been implicated in the development of metabolic syndrome (Ridaura et al., 2013, *Science*, 341, (6150)), cardiovascular disease (Tang and Hazen, 2014, *J. Clin. Invest*, 124, 4204-4211), and cancer (Zitvogel et al., 2015, *Sci Transl Med*, 7, (271)). Accordingly, there is growing appeal for evidence-based nutraceutical strategies targeting the proliferation of healthy "good" microbial species using prebiotics, while simultaneously suppressing the deleterious influence of harmful pathogens.

Most typically, prebiotics comprise soluble and insoluble dietary fiber often found in edible plants, and isolated complex compounds such as galacto-oligosaccharides or fructo-oligosaccharides. Prebiotics are often effective to increase proliferation of the gut microflora. However, many prebiotics will indiscriminately stimulate growth of a variety of bacterial species and so may actually contribute to a less than desirable overall microbiome. Moreover, depending on the type of prebiotic and gut microflora, fermentative degradation of the prebiotic may lead to significant gastrointestinal upset and flatulence.

While a large number of prebiotics have been widely discussed in gut health, postbiotics (i.e., the metabolic byproducts that are responsible for many of the beneficial effects of probiotic microorganisms) may provide more direct and possibly even greater health benefits. For example, the postbiotic butyric acid is a short chain fatty acid (SCFA) typically produced by microorganisms in the colon from undigested portions of fiber (e.g., as found in vegetables). Notably, butyric acid is also a major energy source for the cells lining the colon. However, a concentrated and effective form of dietary butyric acid is not readily straightforward because butyric acid is rapidly absorbed in the upper gastrointestinal tract prior to reaching the colon.

To circumvent absorption issues to at least some degree, the sodium salt of butyric acid (sodium butyrate) can be administered as sodium butyrate is a solid and more stable than the free acid. Orally administered sodium butyrate is able to reach both the small and large intestines where it dissociates to butyrate. However, while at least some of the butyrate will reach the colon, a significant portion of the sodium butyrate is metabolized in the small intestine, thereby decreasing the overall yield of ingested butyric acid. Additionally, the odor of sodium butyrate and butyric acid is often considered foul, making voluntary consumption and marketing difficult.

In other known nutraceutical strategies to help desirable microbial species colonize the intestinal tract, one or more probiotic strains may be ingested, typically in freeze-dried form. Among other suitable probiotic strains, various *Lactobacillus* and *Bifidobacterium* species and their varieties have been reported beneficial in various aspects. However, most of the probiotic strains that are ingested as a dietary supplement (e.g., as a capsule with freeze dried bacteria) will only poorly colonize the colon. Moreover, even if delivered to the colon, probiotic strains may be outcompeted in the colon by other commensal species.

Therefore, even though various pre- and probiotic supplements are known in the art, various disadvantages nevertheless remain. Therefore, there is still a need to provide improved compositions and methods to enhance gut health, especially as it relates to enhancement of desirable *Bifidobacteria* in the gut microbiome.

SUMMARY OF THE INVENTION

The inventive subject matter is drawn to various methods and compositions for increasing the levels of the probiotic *Bifidobacteria* in the gut of a mammal, and preferably a human. The various methods and compositions of the present disclosure include tributyrin-containing as well as tributyrin-enhanced compositions for selectively increasing the levels of *Bifidobacteria* in the gut microbiome of a mammal. Tributyrin-containing compositions include compositions that comprise tributyrin and/or a tributyrin derivative.

In one aspect of the inventive subject matter, the inventors contemplate a method for selectively increasing levels of *Bifidobacteria* in the gut of a mammal that includes providing a tributyrin-containing composition at an effective dosage. An effective dosage may include an amount of tributyrin or a tributyrin derivative of or between 50 mg up to 1,000 mg. Typically, the amount of tributyrin or a tributyrin derivative is between 100 mg up to 500 mg (e.g., 300 mg). Additionally, the tributyrin-containing composition may be processed to mask odor and/or may include at least one odor-masking component. Example processes and components of odor-masking include dextrin complexation and/or lipid complexation. The tributyrin-containing composition may be or may include a tributyrin derivative selected from butyrate mono-ester, butyrate di-ester, beta hydroxybutyrate, monobutyrin, dibutyrin, triacetin, tripropionate, glyceryl monoacetate, glyceryl diacetate, or acetoacetate. In addition to providing a tributyrin-containing composition, the method may also include providing at least one probiotic microorganism selected from *Lactobacillus acidophilus, Lactobacillus casei, Lactobacillus plantarum, Lactobacillus brevis, Lactobacillus gasseri, Lactobacillus rhamnosus, Bifidobacterium lactis, Bifidobacterium breve*, and *Bifidobacterium longum*. Alternatively or in addition to the probiotic microorganism, the tributyrin-containing composition may also include at least one additive selected from superoxide dismutase (SOD), compositions comprising activators of SOD, foods or extracts thereof comprising bioavailable SOD, copper I (Cu I), selenium (Se), fulvic acid, compositions comprising fulvic acid, Co-enzyme $Q_{10}$ (ubiquinone), pyrroloquinoline quinone (PQQ), an arabinoxylan (AX), an arabinoxylan oligosaccharide (AXOS), xylooligosaccharide (XOS), fructooligosaccharide (FOS), galactooligosaccharide (CROS), inulin, pectin, or combinations thereof.

In another perspective, the inventors also contemplate a method of increasing a probiotic benefit of a food item comprising a *Bifidobacterium* strain in which the method includes combining the food item with a tributyrin-containing composition (tributyrin or a tributyrin derivative as disclosed herein) which is present in the food item in an amount that selectively increase the levels of *Bifidobacteria* in the gut upon ingestion of the food item. Additionally, the tributyrin-containing composition in the food item may be processed to mask odor and/or may include at least one odor-masking component as disclosed herein. Also, the tributyrin-containing composition may include an amount of tributyrin or a tributyrin derivative of or between 50 mg up to 1,000 mg or 100 mg up to 500 mg.

In other aspect of the inventive subject matter, the inventors contemplate a dietary supplement including a nutritionally acceptable carrier in combination with a *Bifidobacterium* strain and further comprising tributyrin or a tributyrin derivative as disclosed herein, in which the carrier, the *Bifidobacterium* strain, and the tributyrin or a tributyrin derivative are formulated in a single oral dosage form. Any *Bifidobacterium* strain may be beneficial, and exemplary species include *Bifidobacterium lactis*, *Bifidobacterium bifidum*, *Bifidobacterium infantis*, *Bifidobacterium breve*, and *Bifidobacterium longum*. The single oral dosage form may be a capsule or liquid (e.g., a drink). Additionally, the single oral dosage form may be processed to mask odor and/or may include at least one odor-masking component as disclosed herein. It is also contemplated that the *Bifidobacterium* strain is freeze dried. The single oral dosage form may include *Bifidobacteria* in an amount between $10^6$ and $10^{12}$ CFU/g. As disclosed herein, the tributyrin-containing composition of the single oral dosage may include an amount of tributyrin or a tributyrin derivative of or between 50 mg up to 1,000 mg or 100 mg up to 500 mg.

The inventors further contemplate a composition for increasing levels of *Bifidobacteria* in the gut of a mammal that includes a tributyrin-enhanced *Bifidobacterium* strain which has been grown in a culture medium comprising tributyrin or a tributyrin derivative as disclosed herein. Any *Bifidobacterium* strain may be grown in the presence of tributyrin or a tributyrin derivative, and exemplary species include *Bifidobacterium lactis*, *Bifidobacterium bifidum*, *Bifidobacterium infantis*, *Bifidobacterium breve*, and *Bifidobacterium longum*. After culturing, the composition of the tributyrin-enhanced *Bifidobacterium* may optionally be combined with a tributyrin-containing composition (e.g., tributyrin or a tributyrin derivative). The tributyrin-containing containing composition may include tributyrin or a tributyrin derivative in an amount of or between 50 up to 1,000 mg. The tributyrin-enhanced *Bifidobacterium* strain, the tributyrin or the tributyrin derivative in the culture medium, and/or any tributyrin-containing composition added may each individually or collectively be processed to mask odor and/or may include at least one odor-masking component as disclosed herein. Additionally, the amount of the tributyrin-enhanced *Bifidobacterium* in the composition may be of or between $10^6$ and $10^{12}$ CFU/g. The composition may also include at least one additional probiotic microorganism selected from *Lactobacillus acidophilus*, *Lactobacillus casei*, *Lactobacillus plantarum*, *Lactobacillus brevis*, *Lactobacillus gasseri*, *Lactobacillus rhamnosus*, *Bifidobacterium lactis*, *Bifidobacterium breve*, or *Bifidobacterium longum*. The inventors have also contemplated the composition including at least one additive selected from superoxide dismutase (SOD), compositions comprising activators of SOD, foods or extracts thereof comprising bioavailable SOD, copper I (Cu I) selenium (Se), fulvic acid, compositions comprising fulvic acid, Co-enzyme $Q_{10}$ (ubiquinone), Pyrroloquinoline quinone (PQQ), an arabinoxylan (AX), an arabinoxylan oligosaccharide (AXOS), xylooligosaccharide (XOS), fructooligosaccharide (FOS), galactooligosaccharide (GOS), inulin, pectin, or combinations thereof.

The inventors also contemplate increasing levels of *Faecalibacterium prausnitzii* in the gut of a mammal by administering a tributyrin-containing composition to the mammal. The administration may be ingested in solid or liquid form and the tributyrin-containing composition includes tributyrin or a tributyrin derivative. Methods for increasing levels of *Faecalibacterium prausnitzii* in the gut of a mammal include administering the tributyrin-containing composition to mammals suffering from (e.g., diagnosed with) irritable bowel syndrome and/or Crohn's disease.

Various objects, features, aspects and advantages of the present invention will become more apparent from the detailed description of preferred embodiments of the invention, along with the accompanying drawings.

DETAILED DESCRIPTION

The inventors have now discovered that compositions including a tributyrin or a tributyrin derivative, as well as tributyrin-enhanced compositions confer an increase in the levels of the probiotic *Bifidobacterium* in the colon (large intestine). As used herein, an effect on the levels of *Bifidobacterium* may also be referred to as a "bifido effect."

Tributyrin is a triglyceride and a butyrate ester that may be obtained by formal acylation of the three hydroxy groups of glycerol by butyric acid. As used herein, a derivative of tributyrin includes beta hydroxybutyrate, monobutyrin, dibutyrin, triacetin, tripropionate, glyceryl monoacetate, glyceryl diacetate, acetoacetate, a butyrate mono-ester, and a butyrate di-ester.

The inventors have found that administration of tributyrin confers a remarkable increase in the levels of *Bifidobacterium* found in the gut (e.g., colon) of a subject. To this end, aspects and embodiments of the present invention are directed to methods using and compositions of "tributyrin-containing" compositions and/or "tributyrin-enhanced" compositions, wherein tributyrin-containing compositions include any composition having tributyrin or a tributyrin derivative.

As used herein "subject," "mammal," or "mammal subject" may be used interchangeably to refer to any mammal to which the presently disclosed methods and compositions may be applied or administered. The mammal may have an illness or other disease, but the mammal does not need to be sick to benefit from the presently disclosed methods and compositions. The mammal may be in need of improving its gut and/or overall health, but the mammal may also have a generally healthy gut and desire to maintain or further improve their gut and/or overall health. As such any mammal may consume the disclosed compositions or be a recipient of the disclosed methods. More typically, a mammal as referred to herein includes a human or a domesticated animal. For example, domesticated animals include a dog, cat, or any farm animal including horses, cows, sheep, goats, pigs, or chickens.

As used herein, "administering" and like terms refer to the step of providing to and includes self-administering. Administering of any of the presently disclosed compositions include any mode by which the mammal can ingest the composition. Any suitable means of administration may be used so long as the composition reaches the colon. Accordingly, the form of the composition may be in any form suitable for ingestion to the colon.

Contemplated Methods and Compositions

In one exemplary aspect of the inventive subject matter, the inventors contemplate a method of selectively increasing levels of *Bifidobacteria* in the gut of a mammal with the administration of a tributyrin-containing composition to the mammal at a dosage that increases the relative abundance of *Bifidobacteria* in the gut of the mammal.

Figure 1:
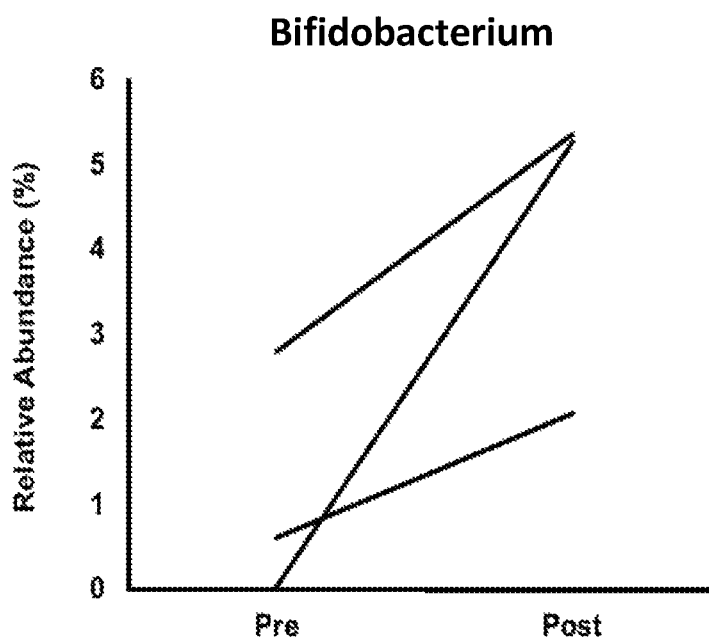
FIG. 1 is a graph of the relative abundance of *Bifidobacterium* before (Pre) and after (Post) a 3-week protocol of 300 mg/daily of tributyrin in three subjects each indicated by a separate line connecting the Pre and Post data points.
Figure 2:
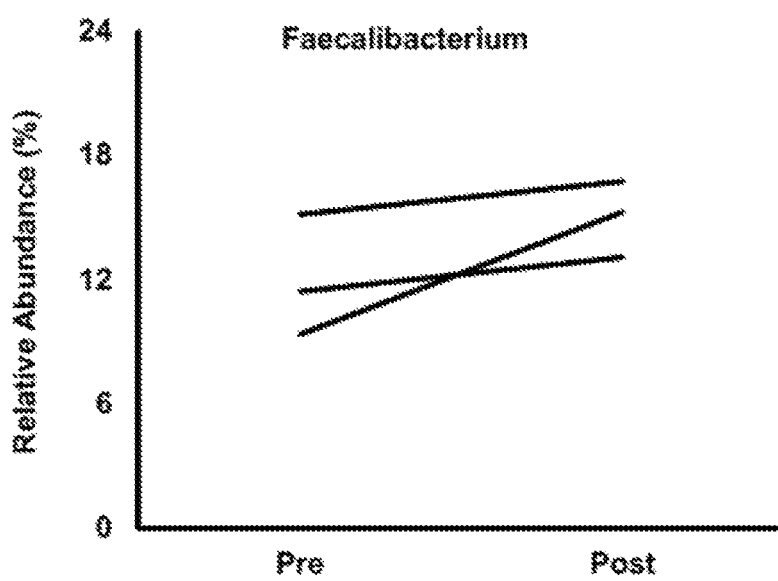
FIG. 2 is a graph of the relative abundance of *Faecalibacterium* before (Pre) and after (Post) a 3-week protocol of 300 mg/daily of tributyrin in three subjects each indicated by a separate line connecting the Pre and Post data points.
Figure 3:
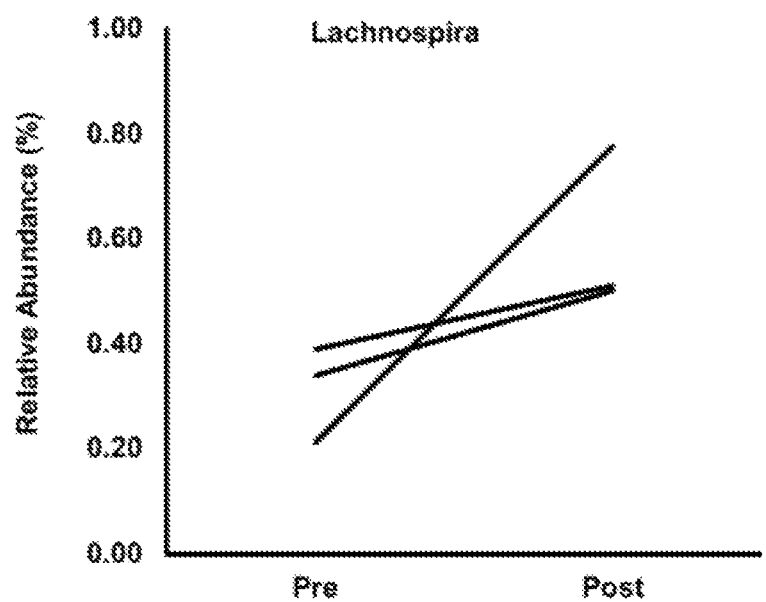
FIG. 3 is a graph of the relative abundance of *Lachnospira* before (Pre) and after (Post) a 3-week protocol of 300 mg/daily of tributyrin in three subjects each indicated by a separate line connecting the Pre and Post data points.

With reference to FIG. 1, tributyrin was taken by each of three volunteers for three weeks, after which time the relative abundance of *Bifidobacterium* was remarkably increased by 8,841%. With reference to FIG. 2 and FIG. 3, the relative abundance (e.g., quantified amounts in a stool sample obtained before the three week study compared to quantified amounts in a stool sample after the three week study) was also increased for *Faecalibacterium* at 29% (FIG. 2) and *Lachnospira* at 114% (FIG. 3). However, the unexpected increase of *Bifidobacterium* indicates a tributyrin-containing composition confers a selective and remarkable increase in *Bifidobacteria*.

Furthermore, the increase in *Faecalibacterium* observed in the colon includes *Faecalibacterium prausnitzii*, the only known *Faecalibacteria* species. Accordingly, a method of increasing the relative abundance of *Faecalibacterium prausnitzii* in the gut of a mammal includes administering to the mammal tributyrin, tributryin-containing compositions, and/or tributryin derivatives in any formulation as disclosed herein for ingestion. The increase in *Faecalibacterium* is particularly advantageous as a low level of this species in the colon has been associated with irritable bowel disease and Crohns' disease. Accordingly, it is contemplated that administration of tributyrin and/or derivatives thereof will increase *Faecalibacterium* in the colon and as such may at least provide symptomatic relief, and in some aspects reduce adverse signs and symptoms of irritable bowel disease and Crohns' disease.

Similarly, a method of increasing the relative abundance of *Lachnospira* in the gut of a mammal includes administering to the mammal in need thereof tributyrin, tributyrin-containing compositions, and/or tributyrin derivatives in any formulation as disclosed herein for ingestion.

Depending on the particular tributyrin-containing formulation and form, contemplated methods include an administration of at least 50 mg/day of tributyrin or a tributyrin alternative. This amount per day may be administered at once or in multiple doses. Typically, an effective amount of tributyrin or a tributyrin derivative in the tributyrin-containing composition to be administered at once or in multiple doses per day is of or between 50 milligrams (mg) to 1,000 mg. The dose or doses may be administered once a day for any period of time. For example, the effective dose may be administered each day for one day, a few days, multiple days, or on a daily basis indefinitely. More typically, the amount of tributyrin or a tributyrin derivative to be administered each day is of or between 100, 200, 300, 400, or 500 mg. Most typically, the amount of tributyrin or a tributyrin derivative to be administered each day is 300 mg.

To further enhance the gut health of the mammal, aspects of the contemplated methods of administering a tributyrin-containing composition include administering at least one probiotic microorganism concomitantly or subsequent to the administration of the tributyrin-containing composition. Any suitable probiotic or multiple probiotics may be combined with the tributyrin-containing composition. Exemplary probiotics include *Lactobacillus acidophilus, Lactobacillus casei, Lactobacillus plantarum, Lactobacillus brevis, Lactobacillus gasseri, Lactobacillus rhamnosus, Bifidobacterium lactis, Bifidobacterium breve,* or *Bifidobacterium longum.*

Multiple forms and formulations of the tributyrin-containing composition are contemplated for selectively increasing the *Bifidobacteria* in the gut. Particularly preferred compositions will be formulated as a nutritional or dietary supplement, in a (medical) food item, in animal feed, or as a pharmaceutical composition in liquid or solid form comprising the tributyrin-containing composition, and may optionally also include a nutritionally or pharmaceutically acceptable carrier. For example, where the composition is in solid form, the compositions may be formulated as a snack bar, yogurt, lozenge, tablet, or capsule, or may be coated onto cereal products, included in baked goods. On the other hand, where the supplement is in liquid form, the compositions may be formulated as a tincture, soft gel capsule, liquid capsule, syrup, carbonated drink, a brewed beverage (e.g., as coffee or tea), a juice, an energy drink, a sports drink, or flavored water. Tributyrin-containing compositions may also be formulated for used in pharmaceutical compositions, typically in combination with a pharmaceutically acceptable carrier where the tributyrin-containing composition is present in an amount to increase levels of *Bifidobacteria* in the gut. While nutritional and pharmaceutical compositions for human use are especially contemplated, it should be appreciated that the tributyrin-containing compositions and formulations may also be employed for veterinary use (e.g., use in animal feed for domestic companion animals ('pets') or in animal feed for farm animals. In further contemplated aspects, the tributyrin-containing composition may also be provided as a bulk product (e.g., in quantities of equal or greater than 100 g, equal or greater than 1,000 g, or equal or greater than 10 kg) for use in production of the nutritional supplement, a (medical) food item, animal feed, or pharmaceutical product.

Viewed from another perspective, tributyrin-containing compositions may also be added to a food item comprising a *Bifidobacterium* strain. The inventors contemplate a method of increasing the probiotic benefit of the food item comprising a *Bifidobacterium* strain by combining or adding a tributyrin-containing composition to the food item. In this way, the tributyrin or tributyrin derivative may be processed by the consumer concomitantly with the *Bifidobacterium* strain in the food item thereby enhancing the probiotic effects. As used herein, a food item includes any solid or liquid form of food or drink that may be consumed or ingested. As disclosed herein, the amount of the tributyrin-containing composition to be added to the food item comprising a *Bifidobacterium* strain may vary depending on the kind and form of the food item. Typically, the amount of the tributyrin-containing composition would be determined on an approximate per serving basis of the food item. More typically, the amount of the tributyrin-containing composition would be of or between 50 mg to 1,000 mg of tributyrin or a tributyrin derivative per serving of the food item. Most typically, the amount of the tributyrin-containing composition would be of or between 100, 200, 300, 400, or 500 mg of tributyrin or a tributyrin derivative per serving of the food item.

Contemplated methods and compositions also include a *Bifidobacterium* grown in the presence of tributyrin or a tributyrin derivative to produce a "tributyrin-enhanced" *Bifidobacterium*. Aspects of this method include the addition of a tributyrin-containing composition to the culture medium of the *Bifidobacterium* strain during fermentation growth. Harvesting of the tributyrin-enhanced *Bifidobacterium* strain may occur at a cell concentration at or between $10^6$ and $10^{12}$ CFU/ml. After harvesting, the isolated tributyrin-enhanced *Bifidobacterium* strain cells may be suspended in a culture or the cells may be processed into an inactivated form (e.g., lyophilized/freeze dried) suitable for incorporation into a capsule or tablet, or as an additive in a food or drink. Additional aspects include combining the isolated tributyrin-enhanced *Bifidobacterium* strain in either the live active culture form or an inactivated form (lyophilized) may be combined with an additional amount of tributyrin or a tributyrin derivative. Typically, the amount of the additional tributyrin or tributyrin derivative is of or between 50 mg to 1,000 mg per $10^6$ and $10^{12}$ CFU/g of tributyrin-enhanced *Bifidobacterium* strain. More typically, the amount of the additional tributyrin or tributyrin derivative is 100, 200, 300, 400, or 500 mg per $10^6$ and $10^{12}$ CFU/g of tributyrin-enhanced *Bifidobacterium* strain. Any suitable probiotic *Bifidobacterium* strain may be grown in the presence of a tributyrin or a tributyrin derivative. Exemplary *Bifidobacterium* species include *Bifidobacterium lactis, Bifidobacterium bifidum, Bifidobacterium infantis, Bifidobacterium breve,* or *Bifidobacterium longum*.

Additional aspects of the inventive subject matter may include adding the tributyrin-containing composition and/or a tributyrin-enhanced composition to a food item as disclosed herein. In a particular example, yogurt or a yogurt drink is a product which already contains bacteria species, such as *Lactobacillus bulgaricus* and *Streptococcus thermophilus*, which are used for fermentation. Accordingly, it is contemplated that yogurt may be supplemented with a tributyrin-containing composition and/or a tributyrin-enhanced *Bifidobacterium* strain for a synbiotic product for gut health.

The inventors also contemplate that any of the presently disclosed tributyrin-containing compositions (e.g., in liquid or solid form or as a nutritional supplement) or tributyrin-enhanced compositions (e.g., a live active or inactive tributyrin-enhanced *Bifidobacterium* strain) may be processed to have a less unpleasant odor, minimal odor, no odor, or an odor that is not unpleasant. To this end, the inventors contemplate the tributyrin-containing and/or the tributyrin-enhanced compositions in a form that reduces or eliminates the native and unpleasant odor of tributyrin. Methods for eliminating, decreasing, and/or masking odors are established in the art. Typically, the tributyrin-containing or tributyrin-enhanced compositions as disclosed herein may be mechanically microencapsulation (e.g., lipid encapsulation) and/or complexed with cyclodextrin or maldextrin as described in U.S. Pat. No. 10,098,964. Further suitable protocols are described, for example, in Al-Kasmi et al., 2017, *J Control Release*, 260, 134-141; Wyspianska et al., 2018, *Food Sci Nutr*, 7, 805-816; and Zheng et al., 2018, *Pharmaceutics*, 10 (157).

For additive bifido effects and in some cases synergistic bifido effects, the presently disclosed tributyrin-containing compositions (e.g., in liquid or solid form or as a nutritional supplement) or tributyrin-enhanced compositions (e.g., a live active or inactive tributyrin-enhanced *Bifidobacterium* strain) may be combined with one or both of the prebiotics of arabinoxylan (AX), an arabinoxylan oligosaccharide (AXOS), xylooligosaccharide (XOS), fructooligosaccharide (FOS), galactooligosaccharide (GOS), inulin, and/or pectin. Certain beneficial effects of these prebiotics have been previously described, e.g., Riviere et al., 2014, *App Env Microbio*, 80, 204-217 and Pandey et al., 2015, *J Food Sci Technol*, 52, 7577-7587.

In another aspect of the inventive subject matter, any of the presently disclosed tributyrin-containing compositions (e.g., in liquid or solid form or as a nutritional supplement) or tributyrin-enhanced compositions (e.g., a live active or inactive tributyrin-enhanced *Bifidobacterium* strain) may be combined with a health additive to increase the breadth of the health benefits. These health additives may be added in any combination with the tributyrin-containing compositions or tributyrin-enhanced compositions depending on the form of the composition as well as consideration for the desired health effect and product cost. Exemplary additives that may be combined with tributyrin-containing compositions or tributyrin-enhanced compositions include superoxide dismutase (SOD), compositions comprising activators of SOD, foods or extracts thereof comprising bioavailable SOD (e.g., sprouted wheat, wheatgrass, encapsulated (lipid and/or protein encapsulation) cantaloupe, rye, barley, barley grass, broccoli sprouts, kale, brussel sprouts, and curcumin (e.g., turmeric), copper I (Cu I), selenium (Se), fulvic acid, foods or extracts thereof comprising fulvic acid (e.g., potatoes, radishes, beets, carrots, root vegetables, blackstrap molasses, and shilajit), Co-enzyme $Q_{10}$ (ubiquinone) or pyrroloquinoline quinone (PQQ).

Figure 4:
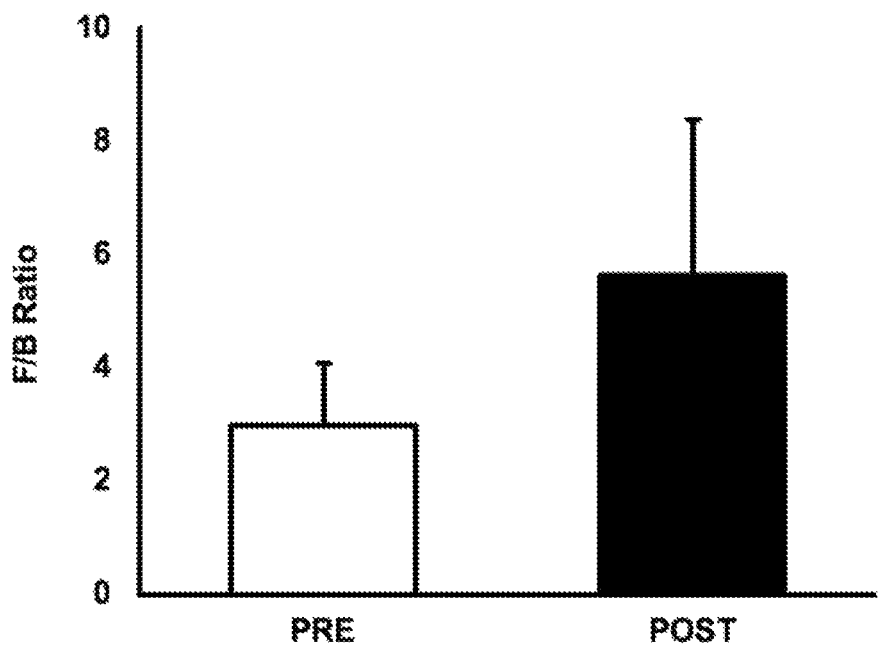
FIG. 4 is a graph of the collective Firmicutes to Bacteroidetes (F/B) ratio in all three of the volunteer subjects before (PRE) and after (POST) a 3-week protocol of 300 mg/daily of tributyrin.

With reference to FIG. 4, the collective ratio of firmicutes to bacteroidetes (F/B ratio) was measured in the stool samples of the three volunteer subjects before and after taking tributyrin daily for three weeks as described in the Examples. The firmicutes and bacteroidetes are each a phylum of bacteria making up the largest portion of the human gut microbiome. In particular the F/B ratio has been reported to be associated with metabolic factors and cardiorespiratory fitness. Durk et al., 2018, *Int J Sport Nutr Exerc Metab*, 29, 249-253. Accordingly, the inventors contemplate a method of increasing the F/B ratio in the gut of a mammal with the administration of a tributyrin-containing composition to the mammal at a dosage that effectively increases the F/B ratio in the gut of the mammal. As shown in FIG. 4, the collective F/B ratios from the three volunteers as measured before and after the study, indicated an increase of approximately 50%. Notably, while previous studies had associated an increased F/B ratio with an increased body mass index (*BMC Microbiol*. 2017; 17:120), such increase was deemed at least in part due to an improved nutrient absorption. As such, contemplated compositions are thought to not only selectively improve gut microflora, but also to enhance nutrient uptake.

EXAMPLES

The inventors recruited three volunteers who were asked to provide some basic anthropometric characteristics and lifestyle habits. All volunteer subjects (2 female and 1 male) were free of chronic disease and reported not having taken an antibiotic within the past six months. Body mass index (kg/m$^2$) analysis classified two of the subjects as "overweight" (BMI>25<30), and one as obese (BMI>30). Although activity habits varied, all of the subjects reported weekly participation in light-to-moderate physical activity, and relatively low caffeine intake (<200 mg/day) and alcohol intake (<3 drinks a week).

Before the start of the 3-week study, stool samples were collected from each of the 3 volunteers using the commercially available UBiome Explorer kit. The collected stool samples were sent to Ubiome labs (San Francisco, Calif.) where DNA was extracted followed by 16S rRNA gene amplification for bacterial classification.

The 3-week study involved each of the volunteers taking 300 milligrams (mg) of tributyrin per day for 3 weeks. Subjects were verbally instructed to maintain usual dietary and physical activity habits throughout the course of the study.

At the end of the 3-week period, stool samples were collected following the same protocol, and sent for analysis.

The bacterial classification analysis was carried out on the stool sample collected before study (PRE) and the stool sample collected after the study (POST) for each of the 3 volunteers.

FIGS. 1, 2, and 3 are each a graph of the change in relative abundance of *Bifidobacteria, Faecalibacterium*, and *Lachnospira*, respectively, found in the PRE stool sample and the POST stool sample where each line represents the change in amount for each volunteer.

FIG. 4 is a graph of the ratio of Firmicutes to Bacteroidetes (F/B ratio) in all three of the PRE study stool samples (left white bar) and all three of the POST study stool samples (right black bar).

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of increasing levels of *Faecalibacterium prausnitzii* in the gut of a human, the method comprising:
   administering a tributyrin-containing composition to the human at a dosage of between 50 to 1,000 mg tributyrin or a tributyrin derivative per day; and
   wherein the tributyrin-containing composition is effective to selectively increase the levels of *Faecalibacterium prausnitzii* in the gut.

2. The method of claim 1, wherein the human suffers from irritable bowel disease and/or Crohn's disease.

3. The method of claim 1, wherein the tributyrin-containing composition further comprises at least one odor-masking component.

4. The method of claim 1, wherein the dosage also increases levels of *Bifidobacteria* in the gut of the human.

5. The method of claim 1, wherein the tributyrin derivative is a butyrate mono-ester, a butyrate di-ester, beta hydroxybutyrate, monobutyrin, dibutyrin, triacetin, tripropionate, glyceryl monoacetate, glyceryl diacetate, or acetoacetate.

6. The method of claim 1, further comprising administering at least one probiotic microorganism selected from the group consisting of *Lactobacillus acidophilus, Lactobacillus casei, Lactobacillus plantarum, Lactobacillus brevis, Lactobacillus gasseri, Lactobacillus rhamnosus, Bifidobacterium lactis, Bifidobacterium breve*, and *Bifidobacterium longum*.

7. The method of claim 1, wherein the tributyrin-containing composition further comprises at least one additive selected from the group consisting of superoxide dismutase (SOD), compositions comprising activators of SOD, foods or extracts thereof comprising bioavailable SOD, copper I (Cu I), selenium (Se), fulvic acid, compositions comprising fulvic acid, Co-enzyme Q10 (ubiquinone), pyrroloquinoline quinone (PQQ), an arabinoxylan (AX), an arabinoxylan oligosaccharide (AXOS), a xylooligosaccharide (XOS), a fructooligosaccharide (FOS), a galactooligosaccharide (GOS), inulin, and pectin.

* * * * *